(12) United States Patent
Castañeda Miranda

(10) Patent No.: US 9,474,778 B2
(45) Date of Patent: Oct. 25, 2016

(54) HERBAL POLYPHARMACEUTICAL FOR PREVENTING AND TREATING ATHEROSCLEROSIS

(76) Inventor: Jose Arturo Castañeda Miranda, Distrito federal (MX)

( * ) Notice: Subject to any disclaimer, the term of this patent is extended or adjusted under 35 U.S.C. 154(b) by 97 days.

(21) Appl. No.: 14/003,991

(22) PCT Filed: Mar. 9, 2012

(86) PCT No.: PCT/MX2012/000026
§ 371 (c)(1),
(2), (4) Date: Nov. 12, 2013

(87) PCT Pub. No.: WO2012/125013
PCT Pub. Date: Sep. 20, 2012

(65) Prior Publication Data
US 2014/0057004 A1    Feb. 27, 2014

(30) Foreign Application Priority Data

Mar. 11, 2011  (MX) .................. MX/a/2011/002765

(51) Int. Cl.
*A61K 36/515* (2006.01)
*A61K 36/37* (2006.01)

(52) U.S. Cl.
CPC ............. *A61K 36/515* (2013.01); *A61K 36/37* (2013.01)

(58) Field of Classification Search
None
See application file for complete search history.

(56) References Cited

U.S. PATENT DOCUMENTS

| | | | |
|---|---|---|---|
| 6,989,165 B2 | 1/2006 | Pushpangadan | |
| 7,074,435 B2 | 7/2006 | Cho | |
| 7,732,410 B2 | 6/2010 | Higuchi | |
| 7,759,393 B2 | 7/2010 | Joerger | |
| 2003/0143290 A1* | 7/2003 | Cho et al. | ..................... 424/728 |
| 2006/0189512 A1* | 8/2006 | Ehrenkranz | ....................... 514/3 |
| 2010/0202980 A1 | 8/2010 | Fogel | |

FOREIGN PATENT DOCUMENTS

| | | |
|---|---|---|
| ES | 2236487 | 7/2005 |
| WO | WO2005070442 | 8/2005 |
| WO | WO2005070442 | 7/2006 |

OTHER PUBLICATIONS

Perez et al., Anti-inflammatory activity of the bark of Hippocratea excelsa, 1995, J Ethnopharmacology, 47: 85-90.*
Andrade-Cetto, A. et al.: 'Mexican plants with hypoglycaemic effect used in the treatment of diabetes.' Journal of Ethnopharmacology vol. 99, No. 3, 2005, ISSN 0378-8741 pp. 325-348.

* cited by examiner

*Primary Examiner* — Terry A McKelvey
*Assistant Examiner* — Catheryne Chen
(74) *Attorney, Agent, or Firm* — Defillo & Associates, Inc; Evelyn A Defillo

(57) ABSTRACT

Herbal MDR for the prevention and treatment of atherosclerosis which includes a summary of the genus *Gentiana* and a summary of the genus *Hippocratea*, in particular, *gentiana lutea* and *hippocratea excelsa*. Comes as a solid, preferably capsules. Herbal composition is obtained by selecting Rhizome and root of *Gentiana lutea* blending by centrifugation, and separating the supernatant which mingles with the alcoholic extract of *Hippocratea excelsa*. Applies in the prevention and treatment of atherosclerosis, as well as in atherosclerotic Occlusive disease complications such as blockage of coronary arteries and arteries that supply the heart.

11 Claims, 2 Drawing Sheets

HERBAL POLYPHARMACEUTICAL FOR PREVENTING AND TREATING ATHEROSCLEROSIS

FIELD OF THE INVENTION

The present invention refers to the field of herbal origin drugs and is particularly directed to the prevention and treatment of atherosclerosis, both in its etiology, their symptoms, as well as in the complications of obstructive atherosclerotic disease in its different modalities, such as blockage of the heart coronary arteries, arteries that irrigate the heart, and other organs where a heart attack may occur, among others. Likewise, the present invention is related to a composition or herbal polypharmaceutical whose constituents develop a synergistic action between themselves, which affects different pathogenic mechanisms of the mentioned disease.

BACKGROUND OF THE INVENTION

U.S. Pat. No. 7,732,410, discloses compositions and methods for the reduction of atherosclerotic plaques. The patent is based on the hypothesis that the presence of mycoplasma and one or more other microorganisms promote the formation of atheroma. The compositions and methods of the patent may also be used to reduce the total level of cholesterol, triglycerides, LDL cholesterol, and HDL cholesterol. In a manner not limited of the invention, the composition comprises a protein capable of removing sialic acid residues, as a neuraminidase enzyme and/or a trans-sialidasa enzyme, a metal chelator, preferably pyrrolidine dithiocarbamate (PDTC), together with one or more purified extracts of plants. One purified plant extract may be derived from a plant selected from the group consisting of *Allium Sativum* (garlic), *Ginkgo Biloba*, tomato, orchids of the genus *Cymbidium* and *Dendrobium*, for example, *Cymbidium* ssp, *Dendrobium Nobile Moschatum*, and *Dendrobium*; guava, ginseng, for example, *Pfaffia Paniculata* (Brazilian ginseng), *Zingiber Officinale* (ginger); and tobacco. The purified extract includes particles that contain DNA or RNA, such as archaea or a nano-archaea. To clarify, this patent cites a product that includes a metal chelator and other products that include plant extracts. It is important to highlight that the patent did not mention a composition with chemical interaction between the extracts of *Gentiana lutea* and *Hippocratea excelsa* to provide novel synergistic effects.

In addition, it is important to highlight that the chelating agent may cause important damage to artery walls, which represents a risk in the use of these products. In addition, the product mentioned in this patent is not able to regulate the behavior of the immune cells involved in the pro-inflammatory process and the genesis of foam cells and thus in the formation of atheroma plaque.

So, a person might think that a chelating agent may 'reduce' the atheroma plaque but would not have a preventive effect on the formation of atheroma plaque nor in the increased pre-existing plaque, or in the formation of new atheroma plaques in the blood system. Furthermore, as it is known, that a chelator can damage the arteries and may not be from repeated use, without causing arterial damage or even an arterial thrombosis. On the other hand, U.S. Pat. No. 6,989,165, discloses to a synergistic pharmaceutical composition useful for the treatment of Hyperlipidemia. The composition comprises plant extracts such as *Kurroo Gentian* of concentration between 2 to 5% by weight, *Murraya Koenigii* in concentration ranging from 8 to 15% by weight, *Allium Sativum* in concentration ranging between 2 and 4% by weight, *Zingiber Officinalis* in concentration ranging between 2 to 5% by weight, *Amorphophallus Campanulatus* in concentration between 1 and 10% by weight, and pharmaceutically acceptable additives. In addition, the patent discloses a process for the preparation of such synergistic pharmaceutical composition and also for the use of the composition for the treatment of Hyperlipidemia, atherosclerosis, and obesity.

More particularly, the U.S. Pat. No. 6,989,165 discloses a compound that includes different plant species, including among them the genus *Kurroo Gentian*. This patent is focused primarily in the lipids metabolism and is available to provide management of Hyperlipidemia, atherosclerosis, and obesity, but it is not clearly defined whether these compounds will work on the pro-inflammatory state, pro-thrombotic, or whether the composition is able to prevent the formation of plaque or can break the plaque. In addition, the patent does not mention the synergistic interaction of components to generate new healing compositions.

The U.S. Patent Publication No. 20100202980, discloses herb based compositions comprising at least one *Urtica* species or an extract of it, at least one *Artemisia* specie, or an extract of it, and an extract of at least one *Morus* specie, wherein the extract is prepared from leaves of *Morus* and includes a *Morus* latex. Also discloses methods for the preparation of these compositions, their use in the treatment and/or prevention of diabetes, hypertriglyceridemia, and related conditions. The patent discloses that conditions associated with Diabetes II include atherosclerosis and indicated the use of *Gentiana Olivieri* as methods of treatment of patients who suffer from these conditions.

US Patent Application Publication No. 20100202980 discloses the combination of different plant species, one of them being the *Gentiana* genus, but a different species (*Olivieri*) and focuses on the metabolic type management of the conditions related to diabetes and hypertriglyceridemia. As in the earlier mentioned patents, this patent does not define its ability to specifically influence the pro-thrombotic status, pro-inflammatory, nor indicates that the combination is effective in the prevention of plaque formation, or that it is able to disintegrate the plaque, as is the case with the present invention which is able to act at all these levels.

U.S. Patent Application Publication No. 20060189512, discloses compositions containing a therapeutically effective amount of extract of phlorizin for the glucose modification in the blood and insulin, facilitate weight loss, prevent weight gain, and provide beneficial effects on the aging process. The patent also discloses a method of treatment of animals with extract of phlorizin, which includes compositions for the treatment of the above-mentioned conditions. These compositions include extracts of *Gentiana Olivieri* or *Hippocratea Excelsa*. Thus, the resulting effects arising from this document again relate to metabolic effects (diabetes management and obesity) and not on the effects on the pathogenic mechanisms of atherosclerosis.

U.S. Pat. No. 7,074,435, discloses a pharmaceutical composition comprising essentially of a base of an extract from herbs such as: *Chaenomelis Fructus, Radix Achyranthis, Acanthopanax, Radix Phlomidis, Radix Gantianae Clematidis Radix*, and includes also an extract from herbs selected from the group consisting of: *Angelicae Radix, Rhizoma Cnidii Gastrodiae Rhizoma*, safflower, *Cinnamomi Cortex*, tear of Job, *Aurantii Nobilis PericapiumRadix Ledebouriellae, Lonicera Japonica, Caulis Akebiae, Caragana Chamlagu*, licorice root, *Incisum Notopterygium, Persicae Semen,*

*Ulmoides Eucommia, Atractylodes Rhizoma, Torilis Japonica, Gentiana radix Gentiana macrophylla, Gentiana maschurica* and *Gentiana lutea*, in combination with other plant extracts for the prevention and treatment of inflammatory diseases and arthritis; which are used for the prevention and treatment of arthritic diseases. The invention also refers to methods for using the previous species extracts and compositions that use them as potent anti-inflammatory and anti-arthritic agents. In this patent document, the disclosed combination is apparently related to the curative management of inflammatory joint diseases, and does not specify to have antiateromatosos effects, antithrombotic effects, nor the obstructive atherosclerotic disease control, in any sense.

Finally, U.S. Pat. No. 7,759,393, discloses a composition containing 1,3-propanediol and an extraction product; 1,3-propanediol in a biological origin composition. The patent also discloses the extraction processes for the extract of a source. These processes include using an ester of 1,3-propanediol and mix the ester 1,3-propanediol with the source. This serves to obtain the extract from the source in the ester. The processes also include separate ester source and the extract. Also discloses compositions containing an ester of 1,3-propanediol and a product of the extraction. In these compositions, the ester may have at least 3% of bio-based carbon. However, this patent does not specify which function or particular effect these compounds may have for the treatment and/or prevention of obstructive atherosclerotic diseases or its complications.

As can be seen, there is currently no development of a similar compound in which the compounds of two plant species synergistically chemically interact in order to obtain a third group of substances that differ from which originated, but even less with the objective of creating a specific treatment for a disease that affects the artery walls.

Thus, it is clear that there have been attempts to attack arterial disease using extracts of plant species, however, these attempts used isolated extracts and never searched for the synthesis of new products created from the combination of extracts of different species. In addition, it has not been researched that certain specific substances exert a synergy effect among them to achieve its unexpected therapeutic effect as it arises in the present invention.

It is important to mention also that in the field of the Chemo pharmacy it includes compounds such as the following to address the problem:

Statins: Although known to reduce hepatic LDL synthesis by inhibition of the HMG CoA reductase, these compounds are hepatotoxic and damage the muscle tissue, in addition they help to reduce the atheromatous plaque thickness up to 5% only after 18 months of treatment and their cost is rather high.

Ezetimibe: This compound inhibits the absorption of cholesterol in the intestine but does not contribute to directly reduce the plaque, in addition it has adverse effects when used concomitantly with statins and has a very high cost.

Fibrates: The fibrates activate the protein lipase that degrades the VLDL and chylomicrons in the liver, releasing its lipidieos components and directing them to the synthesis of HDL. However, they also are hepatotoxic and have a high cost.

Niacin: This compound decreases the LVDL in the liver, lowering the blood triglycerides, but it introduces intolerable side effects to the body such as intense itching, skin rash, etc. They can also generate gastric ulcer and liver damage. Its new forms of presentation for delayed-release are very expensive.

Aspirin: It is a known inhibitor for the plaque aggregation, but it can cause ulcers and bleeding of the digestive tract in people susceptible and/or with long periods of administration.

Clopidogrel: Like many other compounds intended to treat plaque aggregation, this compound is very expensive and produces side effects.

All these drugs, independently and/or combined in different treatment schemes, are used to treat different factors and mechanisms that generate arterial disease, however none of them alone or even combined, significantly reversed the arteries occlusion as proposed by the present invention, due to the synergistic effect that is produced from the blend of herb extracts which results in the arterial repermeabilisations, with non-toxic collateral and side effects, and a very low cost.

As already mentioned, the statins, ezetimibe, fibrates, niacin, aspirin and clopidogrel, in different combinations and treatment schemes, act over some of the mechanisms of the atherosclerotic disease, but not even all of these drugs used together, manage to disintegrate the atheroma plaques and significantly recover the original caliber of the arteries.

In this sense the literature reports that with these treatments and diet, the arteries are repermeabilised up to 5% after 18 months of treatment.

On the other hand, it is relevant to discuss the components that until now have been isolated separately from the two herbal species that are being exposed (*G. lutea* and *H. excelsa*) and the therapeutic effects for which have been used in traditional form and from long ago.

In the case of *Gentiana lutea*, the bibliography reports the following compounds: genciopicrosido, amarogenciosido, Eswerciamarosido, pigments of xanthones, denticina, genciosido, disaccharides (sucrose, gencianosa, genciobiosa), phytosterols, pectin, essential oil.

It is very important to clarify that these compounds have been used traditionally to stimulate digestive secretions, in dyspepsia, fullness, and flatulence. These compounds may present antimicrobial effects in some cases. Never derived from this plant have been proposed in isolated form to treat the pathogenic mechanisms of atherosclerosis.

It is appropriate to comment here that in the crystallization of the extracts of *G. lutea* with identification purposes, yellow crystals are obtained.

The case of *Hippocratea excelsa*, are disclosed below the components that have been isolated by alcoholic extraction. CANOPHYLLOL, CANOFILAL, CANOFILICO, FRIEDELINA, CELASTROL, EXCELSITA acid, PISTIMERINA, TINGENONE, B-CITOSTEROL, HIPOCRATEINA I and II, EMARGINATINA, MAYTEINA, HIPOCRATEINA III.

For the clinical use that has been proposed for the extracts of *hippocratea excelsa* are: anti-inflammatory action, anti-arthritic, anti-carcinogenic, antimicrobial and fungicidal. As in the case of the *Gentiana lutea*, the *H. excelsa* extracts in isolation form has never been proposed for the management of atherosclerosis and never was their use suggested to be in synergistic chemical interaction together with *g. lutea*.

It is important to mention here that the compounds obtained from the combination of both herbal species are predominantly: tannins, flavonoids, terpenes, coumarins and others, which in the bibliographic have not been reported as extracts from these plants, but treated separately.

Finally, it is important to note that patients who, by the extent of damage to their arteries, require invasive or surgical procedures to restore the circulation of their arteries, are subjected to such treatments that are feasible and effective are also extremely risky or costly, being any convenient time preventing these problems using the composition proposed in this invention being an alternative non-invasive, low-cost, clinically tested and made from herbal compounds.

Emphasizing once more is the fact that there is currently no development of a synergistic composition in which chemically interacting compounds from two plant species or herbal, with the purpose of obtaining a polypharmaceutical with new properties and at the same time the composition be very effective when used in the specific treatment for a disease that affects the walls of the arteries.

SUMMARY OF THE INVENTION

An objective of the present invention is to provide an extract composition or polipharmaceuticals from plant species of the *luteal Gentaian e Hippocratea excelsa*, which is subjected to chemical interaction between them, resulting in the synthesis of an herbal polypharmaceutical that synergistically acts over the white blood cells behavior (especially macrophages) at the endothelium level and arteries sub-endothelium, inhibiting platelet aggregation, preventing the oxidation of the LDL small molecules, and hydrolyzing the atheroma plaques formed by the oxidized and calcified cholesterol, giving as a result the revascularization of the arteries, recovering the functionality of the endothelium, and preventing the development of attacks in the heart, brain, and other organs.

Another objective of the present invention is to provide a composition or herbal polypharmaceutical without side effects to the body, for its use in the prevention and treatment of the occlusive atherosclerotic disease in its various forms, such as coronary artery disease, acute heart attack, cerebral vascular events, and other afflictions, such as diabetic foot and secondary erectile failure to the occlusion of the iliac arteries and their branches, which have excellent results in patients who have any of these disorders.

Another objective of the present invention is to provide a polypharmaceutical to be used in the specific care of the arteries, helping to unblock the arteries, and allowing the recovery of the normal function of the arterial endothelium, as well as for use in the prevention of Occlusive atherosclerotic disease, as well as reduce the frequency of heart attacks in various parts of the body.

One objective of the present invention is to provide a polypharmaceutical, which also participates in the reduction of the synthesis of LDL cholesterol and triglyceride, affecting the synthesis of VLDL, at a hepatic level and of the intestine walls.

Moreover, another objective of the present invention, is to provide an alternative non-invasive, of low-cost, clinically tested, and made from herbal compounds, with excellent results in the prevention and treatment of the occlusive atherosclerotic disease.

It is important to clarify that none of extracts of the content in the composition or the herbal pharmaceutical of the present invention, in an independent manner, present the synergistic effect or the benefits provided by the present invention. In addition the use of extracts originally from each plant have completely different effects in the body to the effects proposed by the present invention, meaning that these species used separately as a therapeutic means, have other effects different and unrelated to the prevention and treatment of occlusive atherosclerotic disease.

DETAILED DESCRIPTION OF THE INVENTION

Figure 1:
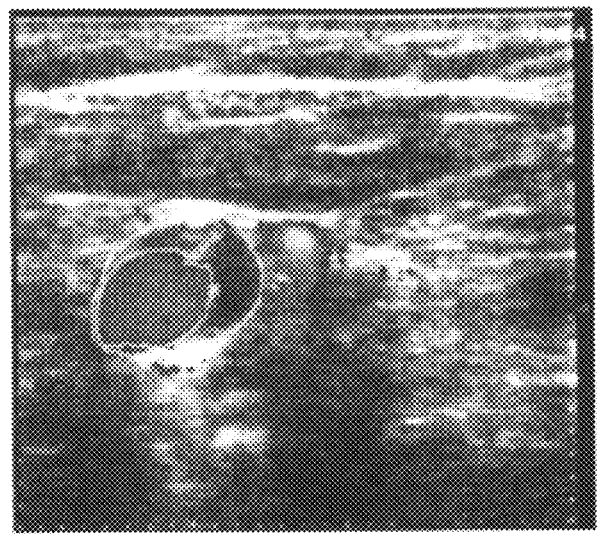
FIG. 1 shows the results of the patient's carotid doppler according to case 1 before showing the results obtained from the treatment with the herbal pharmaceutical, wherein the thickness of atherosclerotic plaque obstructing the arteries of a patient in up to 65%.

The invention is based on the synergistic effect of a composition or herbal polypharmaceutical that includes a first extract of an herb of the *Gentiana* genus and a second extract of an herb of the *Hippocratea* genus and the benefits afforded by the ingestion of a therapeutically effective amount of this composition in the prevention and treatment of Occlusive atherosclerotic disease.

The herb of the *Gentiana* genus is selected from the group consisting of: *Gentiana acaulis Gentiana andrewsii, Gentiana bellidifolia, Gentiana catesbaei, Gentiana cruciata, Gentiana dinarica, Gentiana farreri, Gentiana kurroo, Gentiana lutea, Gentiana macrophyila Gentiana punctata, Gentiana purpurea, Gentiana scabra*, and *Gentiana verna*.

The herb of the *Hippocratea* genus is selected from the group consisting of: *Hippocratea acapulcensis, Hippocratea acuminata, Hippocratea acutiflora, Hippocratea adolphi friderici, Hippocratea affinis Hippocratea celastroides, Hippocratea excelsa*, and *Hippocratea volubilis*.

The herbal extracts of the present invention are subjected to a chemical interaction among them, resulting in the synthesis of an herbal polypharmaceutical that acts in a synergistical manner on the behavior of white blood cells (especially macrophages) at the level of the endothelium, sub-endothelium of the arteries, inhibiting the aggregation of platelets, preventing oxidation of small molecules LDL, and hydrolyzing the atheroma plaques formed by the oxidized and calcified cholesterol, giving as a result the repermeabilisation of the arteries, recovering the functionality of the endothelium, and preventing the development of attacks in the heart, brain and other organs.

Clarifying, the action of the polypharmaceutical is the following:

1. Modulation of the Activity of Monocytes and Other Cells Involved in the Inflammatory Process.

This is obvious from the clinical point of view, since, there is not symptomatic improvement during the initial days, but within weeks of treatment (at least 16 weeks), the atheroma plaques begin to change their physical constitution (start decalcifying) and softening, which can be evidenced by imaging studies.

In addition, the thickness of the arterial endothelium decreases, which indicates that the pro-inflammatory state is decreasing. However, this can also be seen through clinical laboratory determinations, which shows that the high sensitivity PC and other factors that contribute to the attraction migration as well as TNF-alpha, decrease in the blood serum.

Also, it can be mounted invitro testing of the modification in the mechanisms of attraction and rotation of the monoliths and, on the other hand, also tests to demonstrate the neutralization of the effects of peroxidases of the immune cells on small molecules of LDL cholesterol.

2. Inhibition of Platelet Aggregation.

This inhibition is also evident from the clinical point of view, since it has been observed in patients post-heart attack and presenting complicated atheroma plaques in the carotid arteries (fractured), since these patients have survived without developing thrombotic states that produce cerebral vascular events (even in patients already diagnosed as candidates for vascular surgery). It is appropriate to mention that patients in which even the carotid arterial stenosis, caused by the presence of the atheroma plaques produce murmurs phenomens (evident, both acoustically and by arterial doppler), was able to demonstrate that during prolonged treatments (minimum one year, continuous), arterial murmurs disappear, which clinically confirms that the plaques are physically changed and decrease in thickness allowing to restore arterial blood flow.

The inhibition of platelet aggregation can also be assessed by laboratory coagulation tests.

3. Degradation of the Atheroma Plaques.

This has been demonstrated by doing follow-up with imaging studies (color eco doppler) that show a decrease in the thickening of the arterial endothelium, which determine that the pro-inflammatory state is decreasing, also with prolonged treatments (over a year) the atheroma plaques are gradually disintegrating and the caliber of the arteries can be recovered entirety.

On the other hand, invitro tests have been done using lipoprotein complex containing calcium and subjected to oxidation until they acquire a stony consistency, these can be degraded after a few days in contact with the polypharmaceutical of the present invention in solution; the complex is decalcified, the fat saponifies in the liquid phase and is only present a hydrolyzed blood cell of the proteic part of the complex. In this way, it is understood that in the arterial sub-endothelium occurs something similar after the white blood cells are responsible for "cleaning".

After analyzing the above facts, it is logical to understand why the symptomatic effects of the polypharmaceutical, since patients indicated the recovery of general well-being, more energy to develop their activities, and improved tolerance to effort. Even in patients who have already had a coronary event, the angina pectoris crisis disappears and they can gradually be reintegrated into physical exercise, always sticking to the recommendations in the cardiac rehabilitation service. In patients with other conditions, such as diabetic foot, the arterial pulses are recovered and ulcerative lesions can be cured, avoiding amputations. In patients in which the involvement of arteries is at pelvic level and are caused by erectile failure, the use of the drug helps to improve the male erection.

On the other hand, it is essential to clarify that none of the extracts of the content in the composition or herbal polypharmaceutical according to the present invention, in an independent manner, present the effect achieved with the synergy of herbal polypharmaceutical or composition, or the unexpected benefits that this invention provides. In addition, the use of extracts originally from each plant have effects in the body completely different than from those posed by this invention and proposed, meaning that these species used separately as a therapeutic means, have other effects different and unrelated to the prevention and treatment of atherosclerotic occlusive disease and that the resulting synergy of the specific mixture of components for this composition or herbal polypharmaceutical provides results not observed before nor are unexpected.

The composition or herbalist polypharmaceutical of the present invention does not cause side effects for the body, when used in the prevention and/or treatment of atherosclerotic occlusive disease in its different modalities, such as coronary heart disease, myocardial heart attack, cerebral vascular events and other effects, such as diabetic foot and secondary erectile failure to the occlusion of the iliac arteries and their branches, providing excellent results in patients who have any of these disorders. Composition or herbal polypharmaceutical according to the present invention, contains a synergistic blend of herbal extracts, capable of having an impact at different levels of the pathogenesis of the disease atherosclerosis or atherosclerotic occlusive, prevents also the oxidation and accumulation of low density (LDL) cholesterol, beneath the endothelium of the arteries, and preventing the formation of clots that can form when the blood platelets hit against the calcified and fractured atheroma plaques (plates complicated), contributing also to the disintegration of the atheromatous plaque, and reversing the obstruction as much as 100% and controlling the pro-inflammatory and pro-thrombotic states.

The herbal polypharmaceutical according to the present invention reduces the atheroma plaques in its entirety after 18 months of treatment and does so without generating arterial damage. It also contains compounds such as tannins, phenols, terpenes, coumarins and flavonoids, emanating from a synthesis that originates from the chemical interaction between the extracts of *Gentiana lutea* and the *Hippocratea excelsa*, giving thus the polypharmaceutical according to the present invention the ability to influence specifically in the pro-thrombotic, pro-inflammatory states allowing that such combination of herbal extracts to be highly effective in the prevention of plaque formation and even able to disintegrate it. The composition or herbal polypharmaceutical of the present invention is an excellent alternative, non-invasive and inexpensive, made from herbal compounds, which also has been tested clinically with widely satisfactory results in the prevention and treatment of Occlusive atherosclerotic disease.

The way in which the composition of the present invention can be supplied is in the presentation of capsules, since due to the hygroscopic properties of the product is required to encapsulate in a timely manner and kept in dry places. However, it is not limited to the possibility of providing the polypharmaceutical of the present invention in known different presentations.

In general, a therapeutically effective amount is 600 mg once a day for a period of 18 months in the case of unclogging arteries and for the prevention to be planted up to 4 months at different stages.

The scheme of treatment for preventive or curative management of arterial disease ateroesclerosa is as follows: 2 capsules of 300 mg are indicated every 24 hours, taken with some liquid, preferably during the evening and for preventive schemes can last 4-6 months at various stages of life and always monitoring the patient through the valuation of the cholesterol levels, triglycerides, and eventually of apolipoprotein B, and by the estimation of the pro-inflammatory state with the titling of the high-sensitivity CRP. Also with imaging studies highlighting the Doppler color (because of cost and accessibility), but are not outside the helical CT, MRI and angiography for catheterization. Other alternatives of checking the follow-up of the evolution, are: Bruce Protocol stress test and cardiac scintigraphy.

The healing scheme with this product involves taking the treatment for at least a year or more, until showing the disappearance of the atheroma plaques.

In acute cases and as concomitantly with coronary vasodilators and aspirin, may use 4 capsules 300 mg in a single dose.

Below, is an example of the preferred manufacturing of a composition or herbal polypharmaceutical according to the invention. In addition, examples are shown on the implementation of this composition in the treatment of occlusive atherosclerotic disease, as well as on the use in the prevention of.

Manufacturing Process

The manufacturing process involves firstly the decortications of the root and rhizome of the *G. lutea*, by Alkaline hydrolysis, placing in a glass beaker 10 g of root and/or rhizome of *G. lutea* in a solution containing double distilled water including with potassium hydroxide, stirring continuously, to allow the softening of the bark of the root.

Once the above is done, it is then added to the solution acetic acid 80% and mixed to recover the original pH of the plant; the root is peeled, and liquefied in an electric blender having metallic blades (domestic).

Then, the liquefied root is filtered and the product is subjected to centrifugation at 10,000 RPM, using for this purpose a centrifugal clinic for Hanshin for 16 tubes, using test tubes of 10 mi, the supernatant obtained by decantation and then filtered.

Then a hydro-alcoholic extract of 90 g. of the bark of *Hippocratea Excelsa* is prepared. The bark is added to a 30% solution of double distilled water and ethanol of 70°, is subjected to heating at 20° C. to 50° C. Then, it is filtered and finally combined with the filtering of *G. lutea* and both are subjected to heating for 20 minutes at 50° C., while stirring continuously.

This way you get a mixture of both extracts which will undergo a freeze-drying process by which will obtain brown color crystals with bitter flavor, highly hygroscopic, which are encapsulated in gelatin capsules of 300 mg each, which must be kept dry and at room temperature.

Experimental Evidence

For obvious reasons, the casuistry that may be discussed in this section is reduced and it is difficult to obtain the consent of the universe of patients to have a follow-up appropriate of the new and experimental treatment of herbal character and which patients do not have a precise history, nor in terms of information related to its components, or in connection with the successful healing of other patients.

However, in 15 specific patients, a follow-up was able to be performed, based mainly on the clinical evolution and some echo doppler images, as well as in laboratory studies, since although if it had been handled in a very important number of patients, after feeling better and because the lack of economic resource did not continue with the treatment and much less invest in follow-up studies and control, since some of these are expensive. Therefore we will present here the most interesting and representative cases which by adherence to treatment (12 to 18 months) very encouraging results have been obtained regarding the effects of this product.

EXAMPLE 1

It is a patient which currently is 64 years old and was diagnosed in April 1999 as a carrier of atheroma plaques obstructing her carotid arteries by 60% for the left side, with hemodynamic and vascular cerebral insufficiency symptoms impact and 65% to the right side with significant hemodynamic repercussions (report echo doppler dated 28 Apr. 1999), where the photographs show very prominent atheroma plaques that clog up the arterial lumen.

Figure 2:
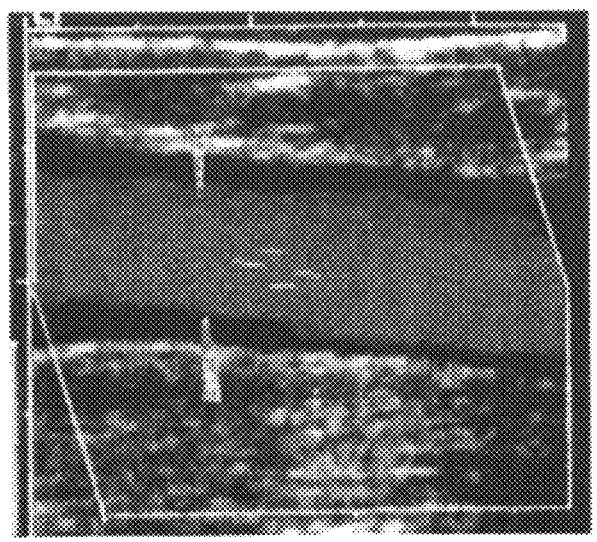
FIG. 2 shows the left carotid artery in the patient of case 1 after 18 months and without presence of atheroma, as a result of the synergic action of the herbal polypharmaceutical according to the claimed invention.

This patient was submitted to treatment with modifications to the diet, increased physical activity and 600 mg of the polypharmaceutical of the present invention were given every night for 18 months. Reports from studies of ECHO doppler of carotid arteries, in November 2000 (FIG. 1) and June 2003 (FIG. 2) show how the atheroma plaques have disappeared entirely, improving the conditions of their arterial flow and what does conclude that arteries are repermeabilised and healed completely. In addition, the patient symptomatically improved 100%.

EXAMPLE 2

It is a patient at 64 years of age and with a history of importance such as 14 years of evolution post heart attack and postoperative lumbar spine at least one year old. The patient maintains active smoking and is diagnosed as a carrier of occlusive atherosclerosis at the level of both carotid arteries, presenting complicated and ulcerated plaques (FIG. 3) since his condition was diagnosed. The patient has been treated irregularly with the herbal polypharmaceutical according to the present invention for periods ranging from a few weeks to 6 months in four stages for enough and appropriate time and to determine the results and effects of the action of the polypharmaceutical.

Figure 3:
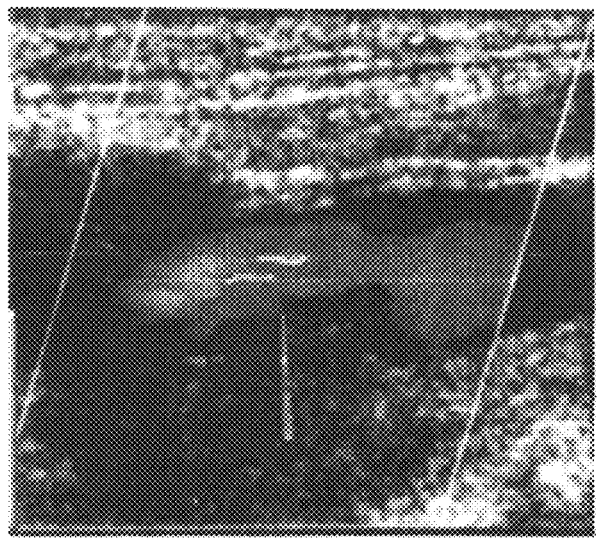
FIG. 3 shows the results of the patient's carotid doppler according to case number 2, showing images of the common right carotid artery and the results of the carotid doppler prior to the administration of the herbal polypharceutical.

As can be seen in FIG. 3, the carotid shows plaque and also presents stenosis of around 30% with flow at its base, indicating this instability and ulceration, reducing also the light caliper of light.

Figure 4:
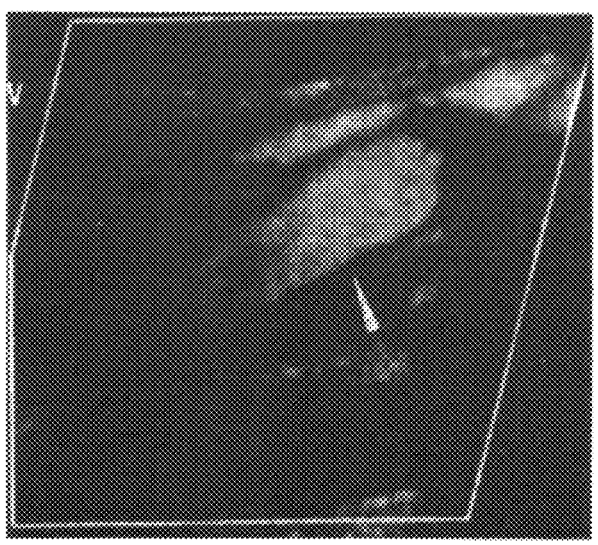
FIG. 4 shows the results of the carotid doppler of the same patient from case 2, once the herbal polypharmaceutical has been administered for a period of about 3 years.

Subsequently, his carotid doppler studies show that the plates evidently decreased, but in addition, the arterial flows have changed significantly and the latest reports mention that there is no ulceration of the plaques (FIG. 4) and that the pro-inflammatory state has been controlled in addition to that the murmur phenomena in the carotid arteries are not already detected to auscultation, i.e., disappeared, which allows to conclude that the arteries are healing.

While only some preferred modalities of the invention have been described so far, the experts recognized that the realization of this invention may be modified and altered without departing from the central spirit and scope of the invention. Therefore, the preferred modality described above must be considered in all aspects as illustrative and non-restrictive. Also, the scope of the invention will be indicated by the subsequent claims more than by the previous description.

The invention claimed is:

1. An herbal composition for prevention and treatment of an atherosclerotic occlusive disease, the herbal composition comprising:
    an alkaline hydrolysis extract of a first herb of the genus *Gentiana*; and
    a hydro-alcoholic extract of a second herb of the genus *Hippocratea*;
    the herbal composition is a solid; and
    the solid is selected from tablets, pills, capsules, or pearls.

2. The herbal composition according to claim 1, wherein the solid is a capsule.

3. The herbal composition according to claim 1, wherein said first herb of the genus *Gentiana* is selected from the group consisting of: *Gentiana acaulis, Gentiana andrewsii, Gentiana bellidifolia, Gentiana catesbaei, Gentiana cruciata, Gentiana dinarica, Gentiana farreri, Gentiana kur-*

*roo, Gentiana lutea, Gentiana macrophylla, Gentiana punctata, Gentiana purpurea, Gentiana scabra*, and *Gentiana verna*.

4. The herbal composition according to claim 1, wherein the first herb of the genus *Gentiana* is *Gentiana lutea*.

5. The herbal composition according to claim 1, wherein said second herb of the genus *Hippocratea* is selected from the group consisting of: *Hippocratea acapulcensis, Hippocratea acuminata, Hippocratea acutiflora, Hippocratea adophi-friderici, Hippocratea affinis Hippocratea celastroides, Hippocratea excelsa*, and *Hippocratea volubilis*.

6. The herbal composition according to claim 1, wherein the second herb of the genus *Hippocratea* is *Hippocratea excelsa*.

7. The herbal composition according to claim 1, wherein a volume of the extract of the first herb of the genus *Gentiana lutea* has a ratio of about 5 to 10% with respect to the extract of the second herb of the genus *Hippocratea excelsa*.

8. The herbal composition according to claim 1, wherein a volume of the extract of the second herb of the genus *Hippocratea excelsa* extract has a ratio of about 90%-95% with respect to the extract of the first herb of the genus *Gentiana lutea*.

9. The herbal composition according to claim 1, wherein the first herb of the genus *Gentiana lutea* extract ratio is around 10% and the ratio of the second herb of the genus extract *Hippocratea excelsa* is approximately around 90%.

10. An herbal composition for prevention and treatment of an atherosclerotic occlusive disease, the herbal composition comprising:
    an alkaline hydrolysis extract of a root and a rhizome of a first herb of the genus *Gentiana;*
    a hydro-alcoholic extract of a bark from a second herb of the genus *Hippocratea;*
    the herbal composition is a solid; and
    the solid is selected from tablets, pills, capsules, or pearls.

11. An herbal composition for prevention and treatment of an atherosclerotic occlusive disease, the herbal composition comprising:
    an alkaline hydrolysis extract of a root and a rhizome of a first herb of the genus *Gentiana*, wherein the alkaline hydrolysis includes a first solution containing distilled water and potasium hydroxide;
    a hydro-alcoholic extract of a bark from a second herb of the genus *Hippocratea*, wherein the hydro-alcoholic extract includes a solution containing distilled water and ethanol;
    the herbal composition is a solid; and
    the solid is selected from tablets, pills, capsules, or pearls.

* * * * *